United States Patent
Terlecki

(10) Patent No.: US 9,861,764 B2
(45) Date of Patent: Jan. 9, 2018

(54) NEEDLE GUIDES SUITABLE FOR PENILE INJECTIONS AND RELATED KITS

(71) Applicant: Wake Forest University Health Sciences, Winston-Salem, NC (US)

(72) Inventor: Ryan P. Terlecki, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 272 days.

(21) Appl. No.: 14/539,538

(22) Filed: Nov. 12, 2014

(65) Prior Publication Data

US 2015/0141961 A1  May 21, 2015

Related U.S. Application Data

(60) Provisional application No. 61/906,602, filed on Nov. 20, 2013.

(51) Int. Cl.
*A61M 5/42* (2006.01)
*A61M 5/32* (2006.01)
*A61M 5/28* (2006.01)

(52) U.S. Cl.
CPC .......... *A61M 5/427* (2013.01); *A61M 5/3287* (2013.01); *A61M 5/28* (2013.01); *A61M 2210/167* (2013.01)

(58) Field of Classification Search
CPC .......... A61B 17/326; A61M 2210/167; A61M 5/427
See application file for complete search history.

(56) References Cited

U.S. PATENT DOCUMENTS

| | | | |
|---|---|---|---|
| 4,228,796 A * | 10/1980 | Gardiner | A61M 5/427 604/116 |
| 4,362,157 A * | 12/1982 | Keeth | A61M 5/427 604/116 |
| 4,642,096 A * | 2/1987 | Katz | A61M 5/427 128/DIG. 6 |
| 5,192,271 A | 3/1993 | Kalb et al. | |
| 5,662,600 A * | 9/1997 | Watson | A61M 27/006 604/8 |
| 5,899,875 A | 5/1999 | Millot et al. | |
| 6,149,625 A | 11/2000 | Weston et al. | |
| 6,319,467 B1 * | 11/2001 | McLernon, III | A61B 90/94 600/556 |
| 8,075,525 B2 * | 12/2011 | Yang | A61M 5/427 604/116 |
| 8,133,201 B1 * | 3/2012 | Hurtado | A61M 5/427 604/116 |
| 2003/0212463 A1 | 11/2003 | Seo | |
| 2008/0154283 A1 | 6/2008 | Shang | |
| 2012/0265138 A1 * | 10/2012 | Harylka | A61M 5/427 604/116 |
| 2012/0303041 A1 | 11/2012 | Marczyk et al. | |
| 2014/0039452 A1 * | 2/2014 | Bangera | G06F 17/5086 604/506 |

OTHER PUBLICATIONS

International Search Report and Written Opinion for corresponding PCT Application No. PCT/US2014/065706, dated Feb. 13, 2015, 16 pages.

* cited by examiner

*Primary Examiner* — Aarti B Berdichevsky
(74) *Attorney, Agent, or Firm* — Myers Bigel, P.A.

(57) ABSTRACT

Embodiments of the invention provide needle guides that facilitate direct penile injection of drug therapies.

17 Claims, 9 Drawing Sheets

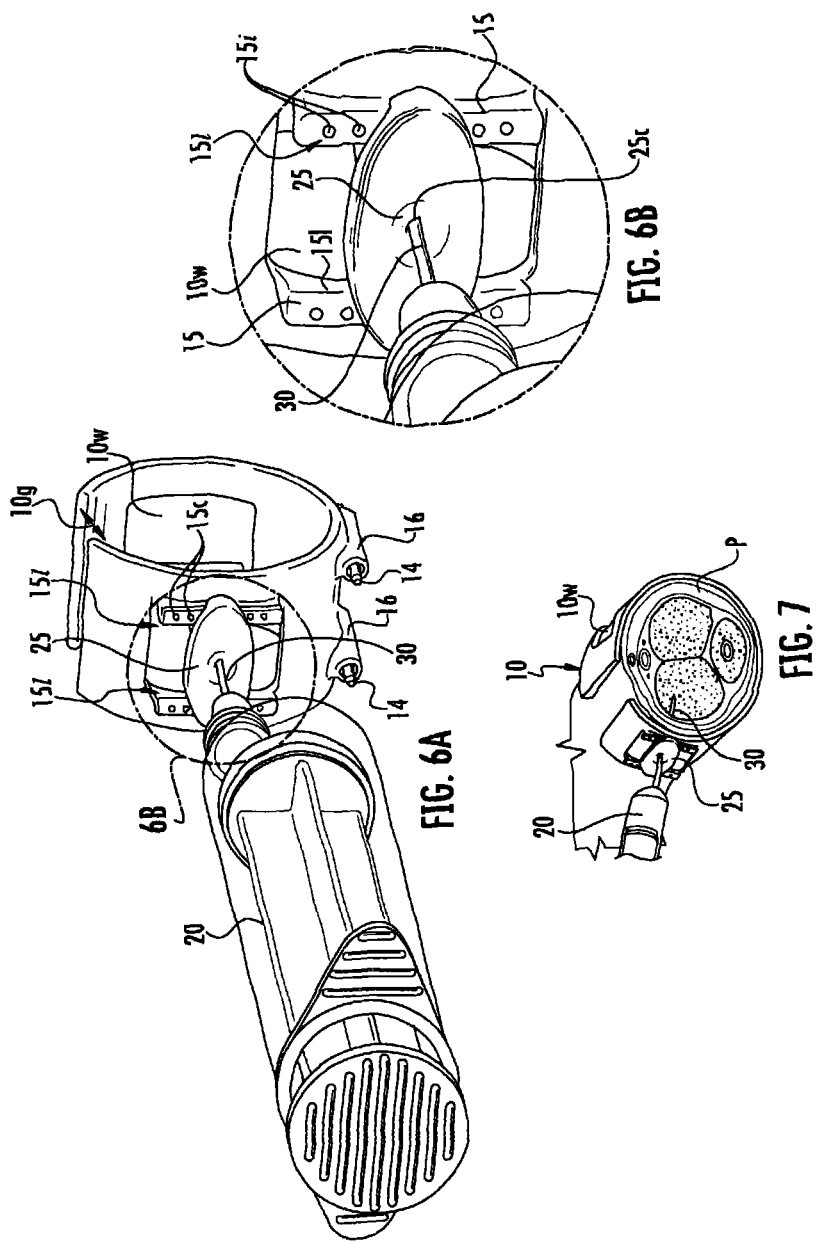

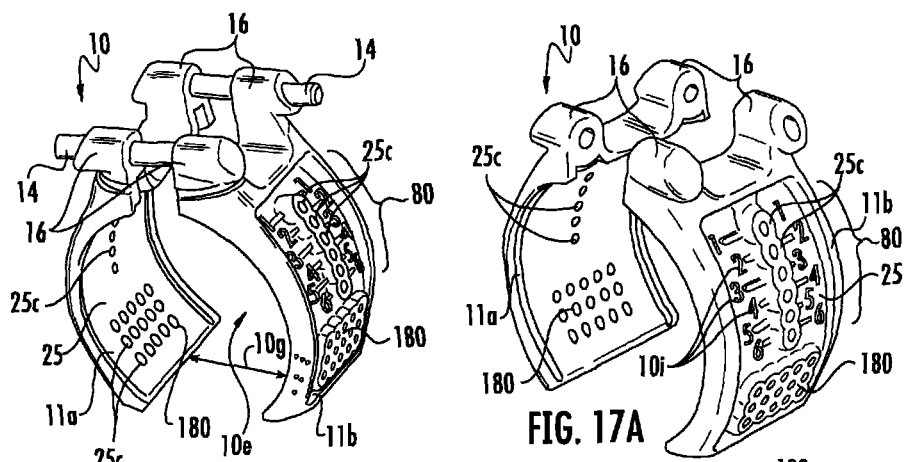

NEEDLE GUIDES SUITABLE FOR PENILE INJECTIONS AND RELATED KITS

RELATED APPLICATIONS

This application claims the benefit of and priority to U.S. Provisional Application Ser. No. 61/906,602, filed Nov. 20, 2013, the content of which is hereby incorporated by reference as if recited in full herein.

FIELD OF THE INVENTION

This invention relates to needle guides for drug therapies.

BACKGROUND OF THE INVENTION

Intracavernous injection therapy is direct injection of a small amount of drug into the corpora cavernosa of a penis. The drug can comprise smooth muscle relaxants that can help increase blood flow into the penis. The advantage of injection therapy is that it does not depend on oral absorption, as pills do.

Currently, the only FDA-approved chemicals for intracavernous injection therapy are Caverject® alprostadil for injection (Pfizer) and Edex® alprostadil for injection from Actient Pharmaceuticals. Both of these agents are prostaglandin $E_1$. Other agents used alone or in combination are papaverine and phentolamine. All three—prostaglandin $E_1$, papaverine, and phentolamine—may be used in combination, and the combination is referred to as "triple P" or "trimix." Prostaglandin $E_1$ and triple P are the two most common forms of injection therapy.

The needle used for the injection is small (typically between about 27-31 gauge) and short. The needle does not need to pierce deeply into the penis to be effective, just into the corpora on one side (e.g., left or right side). The syringe used with the needle is also typically small because the injection volume is usually 1 cc or less. After an initial test dose, usually carried out by the urologist, the urologist will decide on a dose that a patient will use at home (via self-injection or with the help of a partner). It is recommended that the injection not be used more frequently than every 48-72 hours and that successive injections be given to alternate sides of the corpora cavernosa.

SUMMARY OF EMBODIMENTS OF THE INVENTION

Embodiments of the invention provide needle guides that facilitate direct penile injection of drug therapies.

Embodiments of the invention include providing instructional media showing how to use of the needle guide to carry out a direct intracavernous injection.

Embodiments of the invention are directed to needle guides for facilitating needle injection of a flaccid penis.

The needle guides can include a needle guide body comprising a plurality of spaced apart needle guide channels. The needle guide body can be sized and configured to define a longitudinally extending open channel to releasably encase a target region of a (flaccid) penis so that the needle guide channels extend laterally inward to the open channel to allow a tip of a needle to extend through a respective needle guide channel to thereby allow for injection to a proper injection site in the penis held in the needle guide.

The needle guide body can include first and second cooperating members attached together and configured to face each other across the open channel. Each of the first and second cooperating members can have a plurality of the spaced apart needle guide channels.

The first and second cooperating members can have a sidewall with an arcuate inner surface.

The first and second cooperating members can have opposing top and bottom portions. At least one of the top and bottom portions of each of the first and second cooperating members can be laterally slidably attached together to allow for adjustment in size of the open channel.

The first and second cooperating members can have opposing top and bottom portions. Only one of the top and bottom portions of each of the first and second cooperating members can include pins held in pin channels.

The needle guide can have sidewalls that are rigid or semi-rigid. The needle guide channels can have a length to the open channel that is between about 0.1 inches and about 0.5 inches.

Neighboring spaced apart needle guide channels can be spaced apart a vertical distance that is between about 1 mm and 5 mm over both sidewalls.

The needle guide body can be sized and configured so that the open channel has a length that is between 0.5 inches and 2.5 inches.

The needle guide body can define an open, axially extending gap space of between about 0.4 and 0.8 inches and along the top or bottom thereof.

A diameter of the open channel holding a segment of a penis can be between about 1 inch to about 1.75 inches.

The needle guide channels can be sized and configured to releasably accept a needle with a size that is between about 27-31 gauge.

The needle guide can include visual indicia to distinguish different needle guide channels from each other.

The visual indicia, where used, can include at least one of numerals, alphanumerical labels and/or different colors.

The needle guide body can have sidewalls that releasably engage a septum comprising the needle guide channels.

The needle guide can be provided in combination with a container of a pharmaceutical agent for penile direct injection.

Yet other embodiments are directed to kits for direct penile injection. The kits include a needle guide sized and configured to at least partially encase a target segment of a penis. The needle guide can include a plurality of vertically spaced apart needle guide channels. The kits can also include a container of a pharmaceutical agent for penile direct injection.

The kit can also include instructional media for use of the needle guide with a needle to direct inject the pharmaceutical agent in the container.

The needle guide channels can be sized and configured to receive a needle with a size that is between about 27-31 gauge.

The needle guide can have cooperating first and second members that are configured to adjust a diameter of a substantially cylindrical open channel between about 1 inch to about 1.5 inches to encase at least part of a target segment of a respective penis.

Still other embodiments are directed to methods of injecting a penis. The methods include: (a) providing a needle guide with opposing right and left sidewalls, each of the right and left sidewalls comprising a plurality of vertically spaced apart needle guide channels; (b) placing the needle guide about a target region of a flaccid penis; and (c) inserting a needle with a pharmaceutical agent through a needle guide channel; and removing the needle guide.

The inserting step can be carried out to serially alternate inserting a respective needle in needle guide channels on right and left sidewalls to alternate direct injection of the pharmaceutical agent between right and left sides of the penis.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 6A is an enlarged side perspective view of the devices shown in FIG. 1.

FIG. 6B is an enlarged view of the segment 6B shown in FIG. 6A.

FIG. 7 is a schematic illustration of a needle inserted through a needle guide to carry out a direct intracavernous injection.

FIG. 16 is a side perspective view of another embodiment of a needle guide according to embodiments of the present invention.

FIG. 17A is a top, side perspective view of the device shown in FIG. 16 (shown without the attachment pins).

FIG. 17B is a bottom, side perspective view of the device shown in FIG. 17A.

FIG. 17C is a side view of the device shown in FIG. 17A.

FIG. 17D is an end view of the device shown in FIG. 17A.

DESCRIPTION OF EMBODIMENTS OF THE INVENTION

Figure 1:
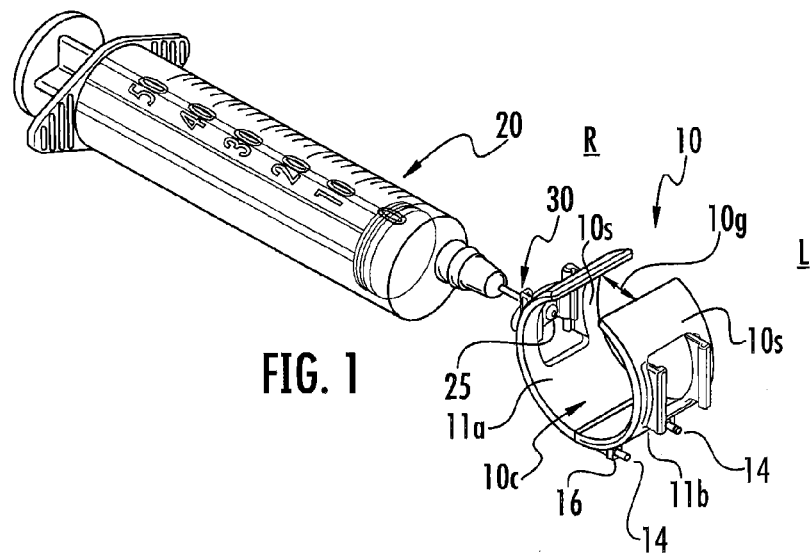
FIG. 1 is a top perspective view of an exemplary needle guide used with a syringe with an injection needle according to embodiments of the present invention.
Figure 2:
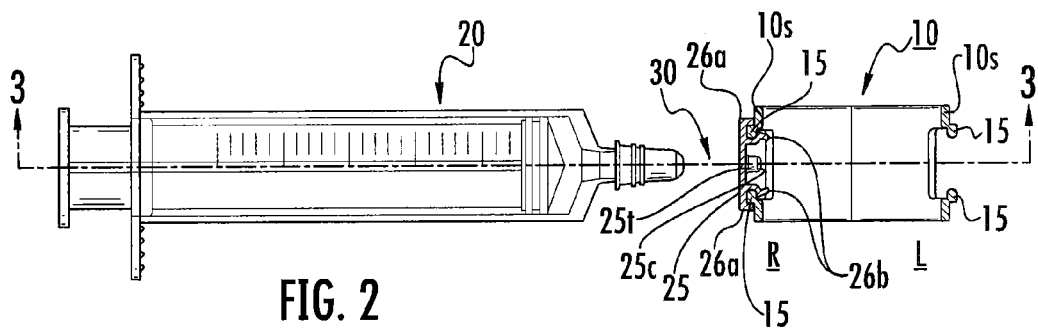
FIG. 2 is a bottom view of the devices shown in FIG. 1.
Figure 3:
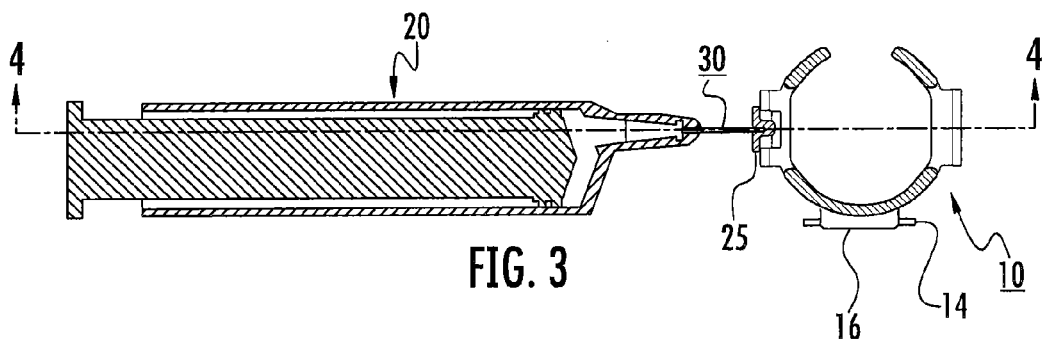
FIG. 3 is a section view taken along line 3-3 in FIG. 2.
Figure 4:
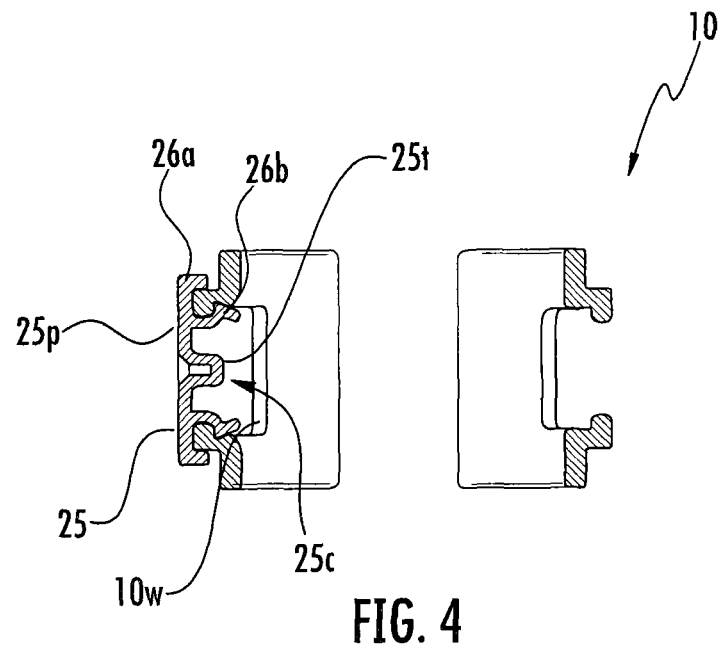
FIG. 4 is a section view taken along line 4-4 in FIG. 3.
Figure 5:
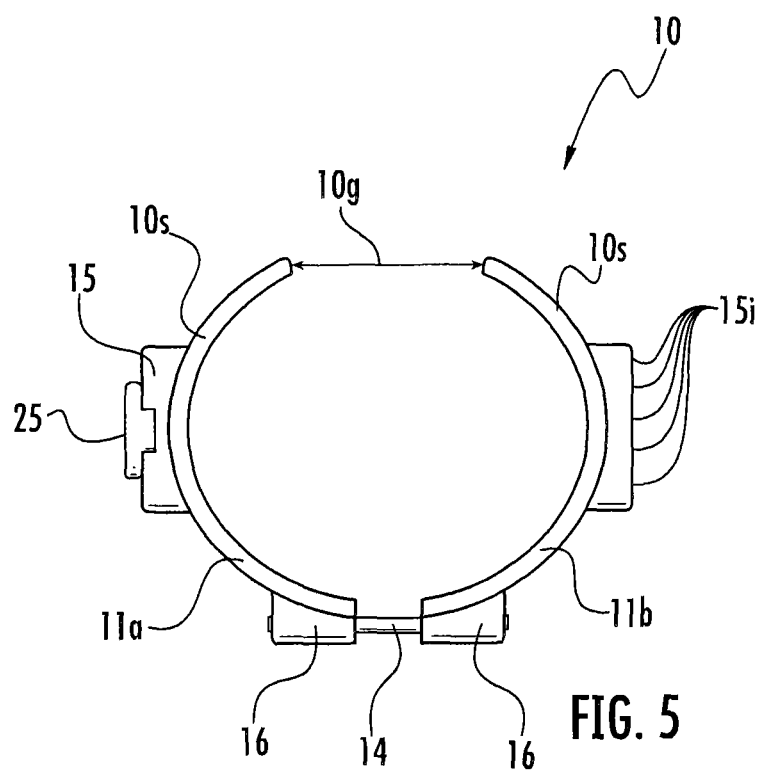
FIG. 5 is an end view of the needle guide shown in the foregoing figures.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments. The term "distal" refers to a direction or location that is closer to or toward a patient while the term "proximal" refers to the opposing direction or a location that is further away from the patient.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

The term "about" means that the recited number or value can vary by +/−20%.

The term "sterile" means that the noted device or material meets or exceeds defined medical guidelines of cleanliness and is substantially (if not totally) without contaminants so as to be suitable for medical uses.

The term "semi-rigid" means that the implant is flexible but has sufficient rigidity to substantially maintain its three-dimensional shape under normal loading.

The term "instructional media" refers to electronic and/or paper manuals, videos, user guides, or the like illustrating and/or describing how to use the needle guide with an injection needle.

The term "septum" refers to a member, feature or device residing between a syringe and a target injection site that is configured to allow an end portion of an injection needle to extend therethrough. The septum can comprise a flexible self-sealing membrane but no affirmative seal is required. The septum can be pre-formed with needle channels and/or may be punctured or pierced by needle tips.

The term "semi-rigid" means the member or device can flex but is configured to be self-supporting and able to retain its shape during use. The term "flexible" means that the member or device is not self-supporting and changes shape from a non-use configuration to a configuration on the body, e.g., it can be rolled or folded.

Referring now to the figures, FIGS. 1-5 illustrate a needle guide 10 configured to releasably cooperate with an injection needle 30. The injection needle 30 is typically held by a syringe 20 of an injectable drug (medication). The drug can be for treating erectile dysfunction. The drug can comprise alprostadil for injection. The drug can be for treating plaque, e.g., a Peyronie's plaque. The drug can comprise collagenase *clostridium histolyticum* (Xiaflex®) or other suitable medication or treatment for direct injection into plaque in the penis.

Figure 8A:
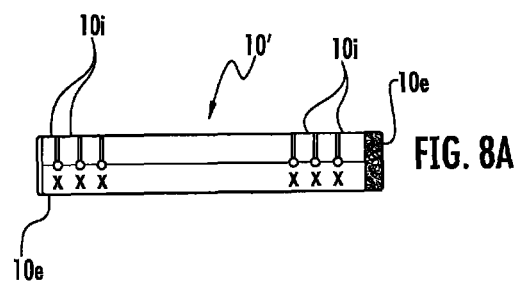
FIGS. 8A-8D are schematic illustrations of alternate embodiments of exemplary needle guides according to embodiments of the present invention.
Figure 8B:
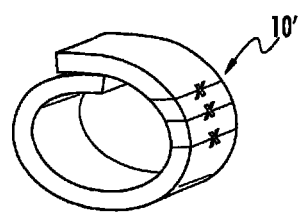

The needle guide 10 can have a substantially cylindrical open axially or longitudinally extending channel 10c sized and configured to receive a target portion of a penis P (FIG. 7). This open channel 10c can be referred to as a holding or support channel. The term "substantially cylindrical" refers to a shape that is configured to at least partially encase a target region of a penis, typically in abutting contact, so that, in operative position, inner surfaces of sidewalls of the needle guide 10s reside against opposing sides of an outer surface of the penis P. The needle guide 10 can be rigid or semi-rigid. The needle guide 10 can be flexible (FIGS. 8A, 8B). The needle guide 10 can have any suitable length but is typically between about 0.25 inches to about 2.5 inches, more typically between about 0.25 to about 1.5 inches. The channel 10c can be provided in any suitable diameter, typically between about 1 inch to about 1.5 inches with or without size adjustment capability.

In some particular embodiments, the needle guide 10 can be provided as two cooperating members 11a, 11b. The two cooperating members 11a, 11b can be laterally adjustable to be closer or further apart for size adjustment of the channel 10c. As shown in FIGS. 1, 3, 5, 13, 14 and 16 the needle guide 10 can include pins 14 that extend in aligned pin channels 16 so that the components 11a, 11b can be slidably laterally extended or retracted (compare FIGS. 1 and 5), typically by about 0.1 inches to about 0.25 inches. The members 11a, 11b can be C-shaped and/or have inner walls that are C-shaped and face each other across the open channel 10c.

The needle guide 10 can include a gap 10g that can be along an upper portion of the device that is sized and configured to allow an ultrasound transducer probe to reside therein. As shown in FIG. 1, for example, this gap 10g can be an open longitudinally extending region between the sides 10s of the device and may have a width that is between about 0.4 and about 0.8 inches, typically about 0.5 inches.

The needle guide 10 can include a septum 25 for allowing the end/tip of the needle 30 to snugly extend therethrough. The septum 25 can be releasably held by sides 10s of the needle guide 10. A user can serially (selectively) mount the septum 25 to a right or left side R, L in alternating order for alternating site injection according to current protocol. Requiring a user to change the side of the septum on the needle guide 10, may act as a reminder as to which different side to use for successive alternating injection sides.

In the embodiment shown in FIGS. 1-6A and 6B, the septum 25 has at least one pre-formed needle channel 25c that snugly receives the end portion of the needle and allows the tip of the needle to extend through a window 10w in the needle guide, then into the injection site.

The septum 25 can comprise a polymeric or elastomeric material. The septum 25 can have sufficient rigidity to be able to guide or support a tip end portion of the needle 30 during injection for proper entry to the injection site. The septum 25 can include at least one open through channel 25c that snugly receives the tip end portion of the needle. The needle guide 10 can include a window 10w under the septum 25 allowing the needle 30 to enter the corpora cavernosa of a penis. The septum 25 can optionally comprise a resilient self-sealing membrane. A line drawn through the axially extending centerline of the channel 25c extends in a direction that intersects an axially extending centerline of the channel 10c.

As shown in FIGS. 1-4, the septum 25 can include a primary body portion with a first thickness and a second, thicker segment 25t defining the channel 25c. This thicker segment 25t can end at a location that is adjacent, flush or slightly beyond the walls of the needle guide at the window 10w at a direction toward the injection site.

The needle guide channels 25c can have a length that is between about 0.1 inches to about 0.5 inches, such as, for example, about 0.1 inches, about 0.15 inches, about 0.2 inches, about 0.25 inches, about 0.3 inches, about 0.4 inches, about 0.45 inches, and about 5 inches. In some embodiments, the needle guide channels 25c have a length that is between about 0.15 and about 0.25 inches.

The septum 25 can be attached to the needle guide 10 at various height positions (e.g., it can be height adjustable) on each side of the needle guide 10. Referring to FIGS. 1, 2, 6A and 6B, in some embodiments, each side 10s of the needle guide 10 can include pairs of axially/longitudinally spaced apart mounting ledges 15 with an inwardly facing lip 15l. The ledges 15 extend upwardly about opposing sides of the window 10w. Pairs of cooperating flexible legs 26a, 26b of the septum 25 attach to respective lip 15l of the needle guide 10 at each spaced apart ledge 15 to hold the septum at a desired height position on the needle guide. The outer surface of the ledges 15 can include alignment indicia 15i such as dots, dimples, numbers, letters or other visual markings for facilitating attachment to a desired height position. The height locking lip regions 15l can be provided as aligned vertically spaced apart positions along the sides 10s of the needle guide 10. However, other attachment configurations may be used that allow for the height positional adjustment of the needle septum 25 relative to the guide 10.

In some embodiments, the needle guide 10 can include a septum 25 affixed to each side 10s of the needle guide. That is, the septum 25 is not required to be releasably attached to the needle guide and/or may be an integral member thereof.

FIGS. 8A and 8B illustrate another embodiment of a needle guide 10'. As shown, the guide 10' can be in the shape of a flexibly configured band to have a first configuration prior to use and a second configuration during use (FIG. 8B). End portions 10e of the band 10' can be releasably attached together. The ends 10e can comprise VELCRO, tape, hooks, bayonet fittings, rails and channels or other attachment configurations. The band 10' can be thin and flexible. Alternatively, the band 10' can have a thickness with sufficient rigidity to provide support for needle entry rather than just be a guide for site selection. The guide 10 can include needle entry indicia 10i. The guide 10' can have the entry location indicia 10i on both sides as shown. Alternatively, the indicia 10i can be on one side and the guide 10' can be put on in a reverse orientation between R and L side uses.

Figure 8C:
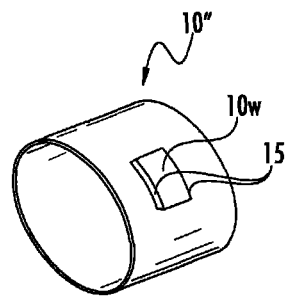

FIG. 8C illustrates that the needle guide 10" can be a closed "collar" type rather than the open shape shown in FIG. 1, for example. A user can slide the collar into position for use.

Figure 8D:
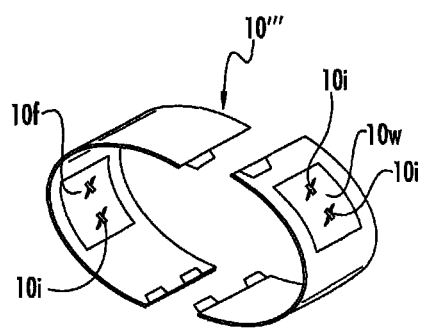

FIG. 8D illustrates that the needle guide 10''' can be provided as matable components that releasably attach together. A user can place each piece on each side of the penis and "snap" or push the components together for use. A septum 25 can be used. Alternatively, as shown, in some embodiments, the guide 10''' can employ a self-sealing (e.g., rubber or polymer) membrane 10f that can be marked with indicia 10i for one or more needle entry locations.

Figure 9:
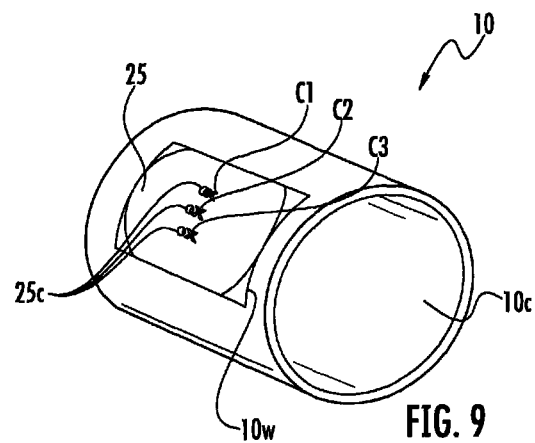
FIG. 9 is a side perspective schematic illustration of another embodiment of a needle guide according to embodiments of the present invention.

As shown in FIG. 9, in some embodiments, the septum 25 can include a plurality of through-channels 25c and a user can select an appropriate one for injection. Where the septum 25 has a plurality of user selectable channels 25c, an appropriate channel 25c can be identified at initial use (e.g., at an urologist's office) and marked for future reference. The different channels 25c can be color-coded and/or numbered by position, e.g., C1, C2, C3, so that a user can visually identify which channel to use when at home. e.g., green for position/level 1, blue for position/level 2 and the like.

Figure 10:
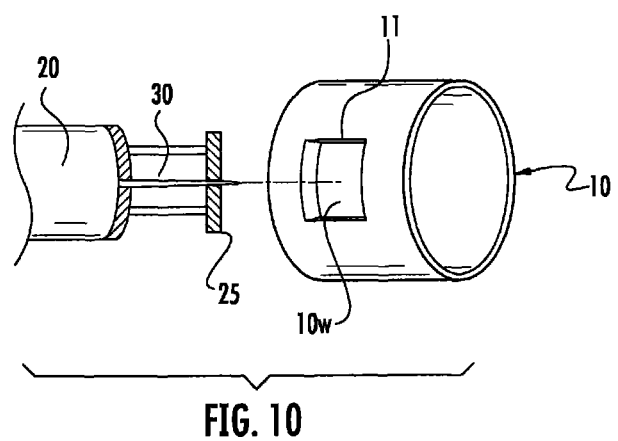
FIG. 10 is a schematic illustration of another embodiment of a needle guide configuration according to embodiments of the present invention.

As shown in FIG. 10, the septum 25 can be attached to the syringe or needle rather than the needle guide 10. In use, the septum abuts an interface region 11 on the needle guide thereby allowing injection and providing guidance and support.

Figure 11:
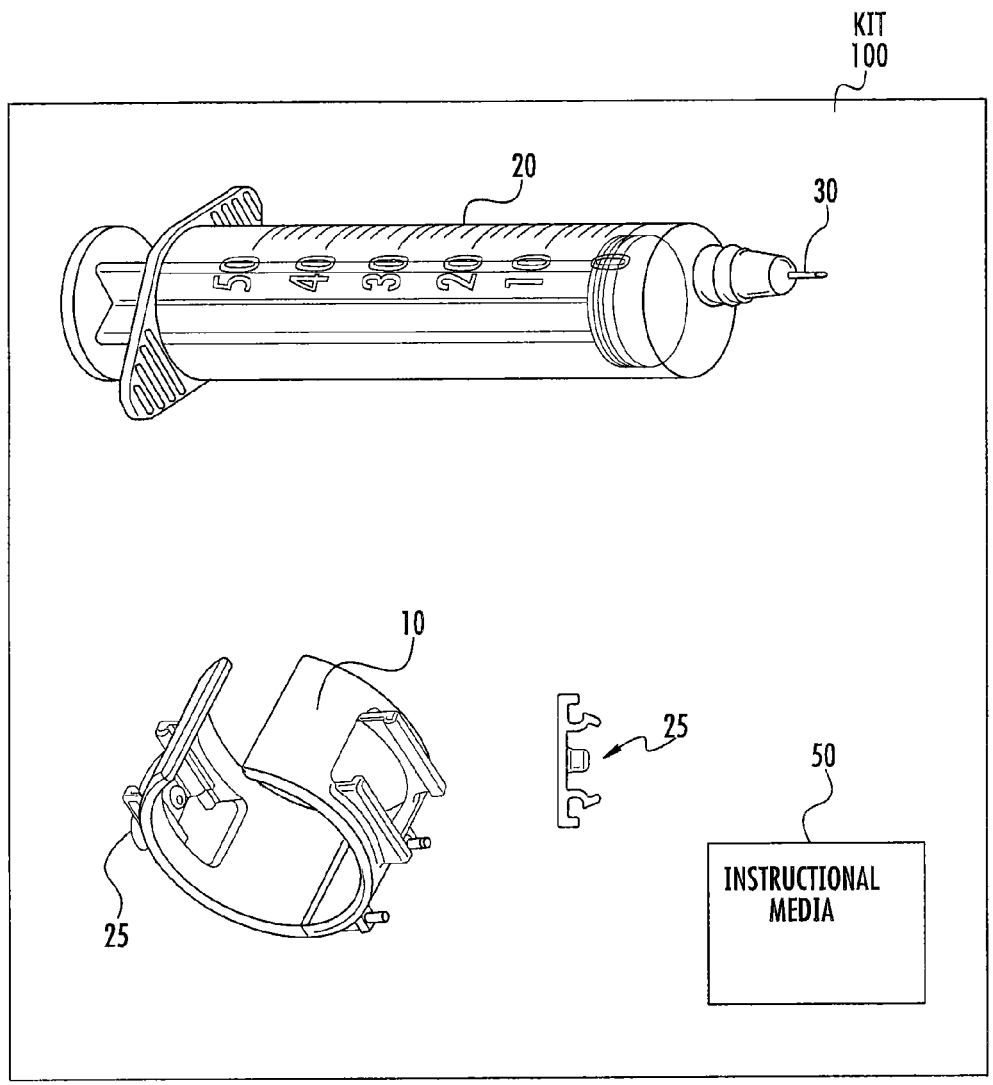
FIG. 11 is a schematic illustration of a kit for direct intracavernous injection according to embodiments of the present invention.

FIG. 11 illustrates that the needle guide 10 can be provided in a kit 100 with the syringe 20 with the drug therapy. Optionally, instructional media 50 can be included in the kit 100. The needle assembly 10 can have at least one septum 25. In some embodiments, the kit can include a plurality of discrete septums 25

Figure 12:
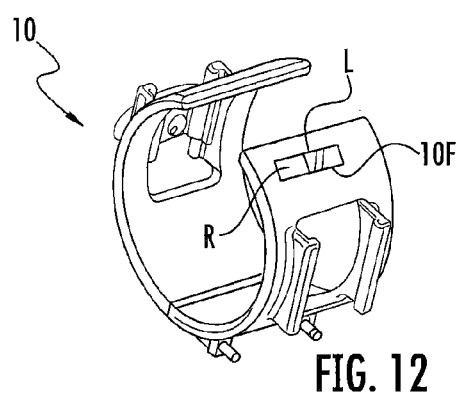
FIG. 12 is a schematic illustration of another embodiment of a needle guide according to embodiments of the present invention.

FIG. 12 illustrates that the needle guide 10 can include onboard reminder member 10F that can be moved by a user. For example, a flag or other member that can be moved to show a "R" or "L" character which can act as a visual reminder as to which side the last injection was made "R" or "L" or as to which side the next injection is to be made on.

Similar to the embodiment shown in FIG. 1, FIGS. 13, 14 and 16 illustrate the needle guide 10 can have two cooperating components that can have cooperating members 11a, 11b that can define a substantially cylindrical channel 10c for holding the penis P. In use, the device 10 is typically oriented with the pins 14 positioned under the penis (e.g., the gap 10g above the penis), but the needle guide 10 can be used in the reverse orientation. The members 11a, 11b can have sidewalls with an inner surface that is arcuate and/or C-shaped that face each other across the channel 10c.

The two components 11a, 11b can be laterally adjustable to be closer or further apart for size adjustment of the channel 10c. As shown, the needle guide 10 can include pins 14 that extend in aligned pin channels 16 so that the components 11a, 11b can be slidably laterally extended or retracted, again, typically by about 0.1 inches to about 0.25 inches.

Figure 13:
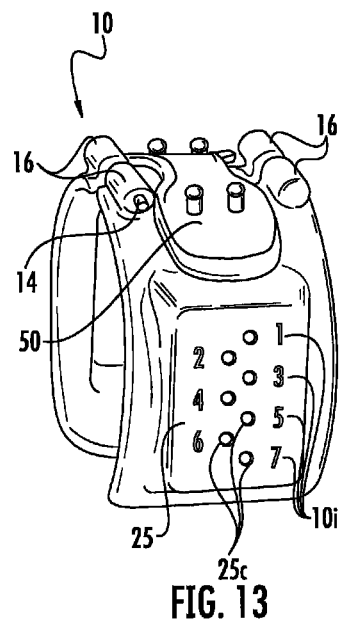
FIG. 13 is a side perspective view of yet another embodiment of a needle guide according to embodiments of the present invention.
Figure 14:
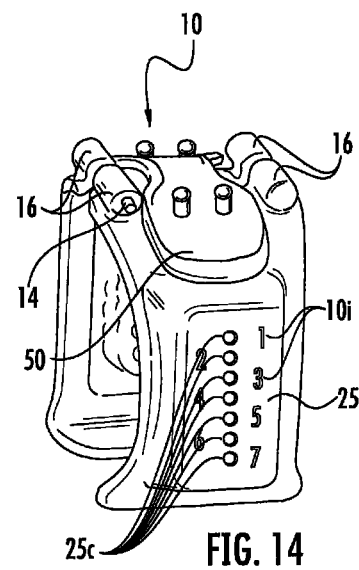
FIG. 14 is a side perspective view of another embodiment of a needle guide according to embodiments of the present invention.
Figure 15A:
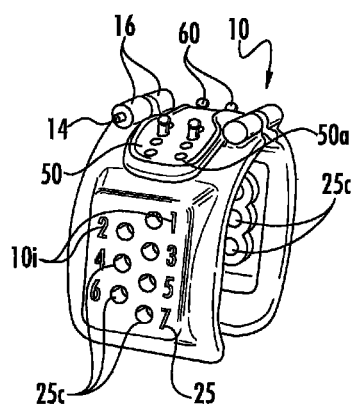
FIG. 15A is a side perspective view, opposing the side shown in FIG. 13, according to embodiments of the present invention.
Figure 15B:
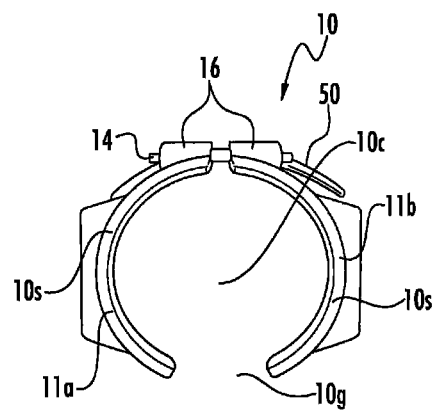
FIG. 15B is a top, end view of the device shown in FIGS. 13 and 15A.
Figure 15C:
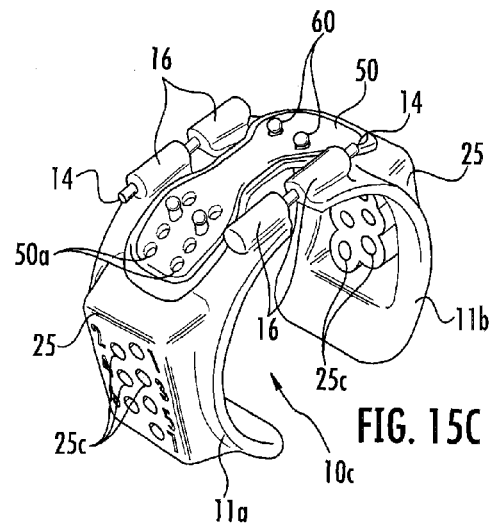
FIG. 15C is a bottom, end perspective view of the device shown in FIG. 15A.
Figure 15D:
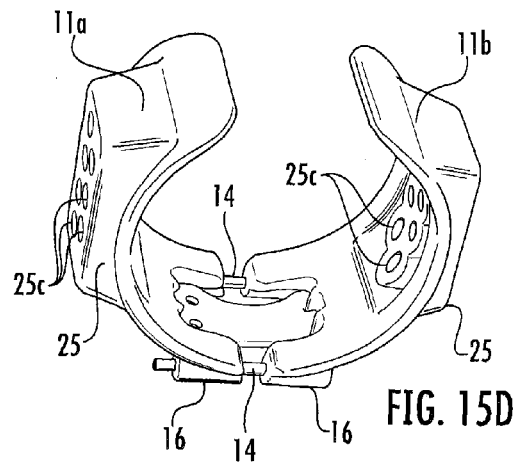
FIG. 15D is an end perspective view of the device shown in FIG. 15A.
Figure 15E:
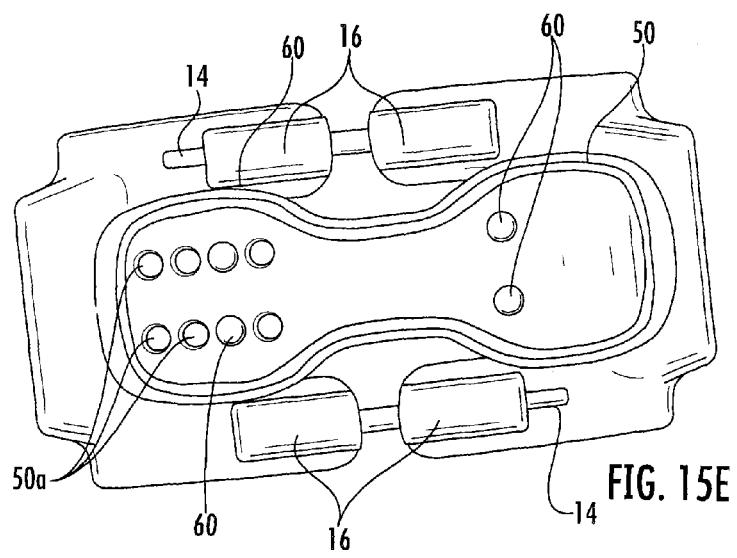
FIG. 15E is a top view of the device shown in FIG. 15A.

FIGS. 13 and 15A-15E, illustrate the needle guide 10 with needle guide channels 25c arranged in a plurality of adjacent columns. Although shown as two adjacent columns in FIG. 13, more than two columns may be used. Also, the needle guides 25c may be arranged in a single column. An example of a single column arrangement is shown in FIG. 14. The needle guide channels 25c can be identified with channel indicia 10i including numbers. FIG. 13 shows the adjacent columns of needle guide channels 25c can be configured so that a needle guide channel in one column is offset to reside at a horizontal height location that is between neighboring needle guide channels in the other column. In both FIGS. 13 and 14, there are seven (7) needle guide channels 25c, numbered as such, on each side 11a, 11b, but more or less needle guide channels 25c may be provided with the same number on each side 11a, 11b or different numbers on each side of the needle guide 10. For example, the needle guide 10 can have between 5-30 needle guide channels on each side (not shown).

FIGS. 13 and 14 also illustrate that the needle guide 10 may optionally include a yoke 50 (which may also be termed a collar) that attaches to the needle guide 10 between pins 14 to hold the two sides 11a, 11b in a desired position. The yoke 50 can include a plurality of apertures 50a that can be selected to provide the desired position of the two sides 11a, 11b. The outer end portion of the needle guide 10 can include upwardly extending posts 60 that can extend through respective apertures to releasably engage or detachably secure the yoke 50. Other attachment members or configurations may be used including, for example, VELCRO, tape, and the like.

FIGS. 16 and 17A-17D illustrate that the needle guide 10 can include needle guide channels 25c with visual indicia 10i comprising a sequence of numbers, shown as 1-6. In this embodiment, the needle guide 10 may include a first set 80 of needle guide channels 25c and a second set 180 of needle guide channels 25c. The second set 180 can be positioned under (FIG. 17A) or over (FIG. 17C) the first set 80, depending on the orientation of the device 10, the first set. The first set 80 of needle guide channels 25c can be sized and configured to receive needles that inject therapies for treating plaque while the needle guide channels 25c are sized and configured to treat ED. The first set 80 of needle guide channels 25c can be arranged to extend in one or a plurality (e.g., two) of columns over a height distance that is between about 10-15 mm, such as about 10 mm, about 10.5 mm, about 11 mm, about 11.5 mm, about 12 mm, about 12.5 mm, about 13 mm, about 13.5 mm, about 14 mm, about 14.5 mm, and about 15 mm. Neighboring needle guide channels 25c can be spaced apart laterally and/or vertically by between about 1-5 mm, such as about 1 mm, about 1.5 mm, about 2 mm, about 2.5 mm, about 3 mm, about 3.5 mm, about 4 mm, about 4.5 mm, and about 5 mm, for example, in some embodiments.

The second set 180 of needle guide channels 25c can occupy a shorter height distance, that is typically less than half the height distance, of the first set 80. In some embodiments, the second set 180 can extend over a height distance that is about 5 mm and a width distance that is the same or greater than the height distance, such as, for example, between about 5-20 mm, typically between about 10-20 mm. Neighboring needle guide channels 25c in the second set 180 can be laterally and/or vertically spaced apart by between about 1-5 mm, such as about 1 mm, about 1.5 mm, about 2 mm, about 2.5 mm, about 3 mm, about 3.5 mm, about 4 mm, about 4.5 mm, and about 5 mm, for example, in some embodiments.

The needle guides 10, 10', 10", 10''' can be single use or reusable at least over a defined treatment period (typically the latter). The septum 25, where separate, can be single use or reusable (typically the latter).

Embodiments of the invention can provide the following functions/benefits:
1. Precise delivery of a pharmacologic agent
2. Safety of delivery
3. Reproducibility for patients and/or providers
4. Easier injection by stabilizing a penis
5. The ability to accommodate ultrasound guidance
6. Reusable
7. Can be individualized to a patients anatomy and chosen level of injection The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A needle guide for facilitating a needle injection into a penis, comprising:
   a needle guide body comprising a plurality of spaced apart needle guide channels, the needle guide body sized and configured to define a longitudinally extending open channel to releasably encase a target region of a penis so that the needle guide channels extend laterally inward toward the longitudinally extending open channel to allow a tip of a needle to extend through a respective needle guide channel to thereby allow for injection to a proper injection site in the penis held in the needle guide,
   wherein the needle guide body comprises first and second cooperating members attached together, wherein the first and second cooperating members have opposing top and bottom portions, and wherein at least one of the top and bottom portions of the first and second cooperating members are coupled to at least one laterally extending pin, and wherein at least one of the top and bottom portions of each of the first and second cooperating members are laterally slidably attached together via the at least one laterally extending pin to allow for adjustment in size of the open channel.

2. The needle guide of claim 1, wherein the first and second cooperating members face each other across the open channel, and wherein each of the first and second cooperating members having a plurality of the spaced apart needle guide channels arranged in an array of vertically and/or longitudinally spaced apart needle guide channels.

3. The needle guide of claim 1, wherein the first and second cooperating members have a sidewall with an arcuate inner surface and a planar outer surface portion, and wherein at least some of the needle guide channels extend through the planar outer surface portion to exit through the arcuate inner surface.

4. The needle guide of claim 1, wherein the first and second cooperating members of the needle guide body define sidewalls that are rigid or semi-rigid, and wherein the needle guide channels have a length from an outer facing edge of thereof to the open channel that is between about 0.1 inches and about 0.5 inches.

5. The needle guide of claim 1, wherein neighboring spaced apart needle guide channels of the needle guide channels are spaced apart a vertical distance that is between about 1 mm and 5 mm over sidewalls of both the first and second cooperating members.

6. The needle guide of claim 1, wherein the needle guide body is sized and configured so that the open channel has a length that is between 0.5 inches and 2.5 inches.

7. The needle guide of claim 1, wherein the needle guide body defines an open, longitudinally extending gap space of between about 0.4 and 0.8 inches along a top or bottom thereof.

8. The needle guide of claim 1, wherein a diameter of the open channel is between about 1 inch to about 1.75 inches.

9. The needle guide of claim 1, wherein the needle guide channels are sized and configured to releasably accept a needle with a size that is between about 27-31 gauge, and wherein each of the first and second cooperating members have a plurality of the needle guide channels with at least some arranged to be vertically spaced apart.

10. The needle guide of claim 1, wherein the first and/or second cooperating member of the needle guide body comprises sidewalls that releasably engage an external septum that is held by spaced apart neighboring segments of the sidewalls, wherein the external septum comprises the needle guide channels.

11. The needle guide of claim 1 in combination with a container of a pharmaceutical agent for penile direct injection, and wherein at least one of the needle guide channels has a different diameter than other needle guide channels.

12. The needle guide of claim 1, further comprising visual indicia to distinguish different needle guide channels from each other.

13. The needle guide of claim 12, wherein the visual indicia comprises at least one of numerals, alphanumerical labels and/or different colors.

14. A method of injecting a penis, comprising:
   providing the needle guide of claim 1;
   placing the needle guide about a target region of a flaccid penis; and
   inserting a needle with a pharmaceutical agent through a needle guide channel in the needle guide; and
   removing the needle guide from the penis.

15. The method of claim 14, wherein the inserting step is carried out to serially alternate inserting a respective needle in needle guide channels on right and left sidewalls to alternate direct injection of the pharmaceutical agent between right and left sides of the penis.

16. A needle guide for facilitating a needle injection into a penis, comprising:
   a needle guide body comprising a plurality of spaced apart needle guide channels, the needle guide body sized and configured to define a longitudinally extending open channel to releasably encase a target region of a penis so that the needle guide channels extend laterally inward toward the longitudinally extending open channel to allow a tip of a needle to extend through a respective needle guide channel to thereby allow for injection to a proper injection site in the penis held in the needle guide,
   wherein the needle guide body comprises first and second cooperating members attached together, wherein the first and second cooperating members have opposing top and bottom portions, and wherein at least one of the top and bottom portions of the first and second cooperating members are coupled to at least one laterally extending pin,
   wherein the first and second cooperating members face each other across the open channel, and wherein each of the first and second cooperating members having a plurality of the spaced apart needle guide channels arranged in an array of vertically and/or longitudinally spaced apart needle guide channels,
   wherein at least one of the top and bottom portions of each of the first and second cooperating members are laterally slidably attached together via the at least one laterally extending pin to allow for adjustment in size of the open channel, and wherein the array of needle guide channels is configured with both vertically spaced apart and longitudinally spaced apart needle guide channels.

17. A needle guide for facilitating a needle injection into a penis, comprising:
   a needle guide body comprising a plurality of spaced apart needle guide channels, the needle guide body sized and configured to define a longitudinally extending open channel to releasably encase a target region of a penis so that the needle guide channels extend laterally inward toward the longitudinally extending open channel to allow a tip of a needle to extend through a respective needle guide channel to thereby allow for injection to a proper injection site in the penis held in the needle guide,
   wherein the needle guide body comprises first and second cooperating members attached together, wherein the first and second cooperating members have opposing top and bottom portions, and wherein at least one of the top and bottom portions of the first and second cooperating members are coupled to at least one laterally extending pin,
   wherein the first and second cooperating members face each other across the open channel, and wherein each of the first and second cooperating members having a plurality of the spaced apart needle guide channels arranged in an array of vertically and/or longitudinally spaced apart needle guide channels,
   wherein the first and second cooperating members are laterally slidably moveable to adjust a size of the longitudinally extending open channel using the at least one laterally extending pin held in a laterally extending pin channel, and wherein the at least one laterally extending pin includes at least first and second longitudinally spaced apart laterally extending pins that are parallel to each other and perpendicular to an axially extending centerline of the longitudinally extending open channel.

* * * * *